US010113197B2

(12) United States Patent
Sun et al.

(10) Patent No.: US 10,113,197 B2
(45) Date of Patent: Oct. 30, 2018

(54) PURIFIED POLYMERASE / TEMPLATE COMPLEXES

(71) Applicant: Pacific Biosciences of California, Inc., Menlo Park, CA (US)

(72) Inventors: Lei Sun, San Jose, CA (US); Insil Park, Fremont, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 45 days.

(21) Appl. No.: 14/568,627

(22) Filed: Dec. 12, 2014

(65) Prior Publication Data

US 2015/0167072 A1 Jun. 18, 2015

Related U.S. Application Data

(63) Continuation of application No. 13/233,585, filed on Sep. 15, 2011, now Pat. No. 8,936,911.

(60) Provisional application No. 61/385,376, filed on Sep. 22, 2010.

(51) Int. Cl.
*C12Q 1/68* (2018.01)
*C12Q 1/6869* (2018.01)
*C12N 9/96* (2006.01)
*C12P 19/34* (2006.01)
*C07H 21/02* (2006.01)

(52) U.S. Cl.
CPC .............. *C12Q 1/6869* (2013.01); *C12N 9/96* (2013.01); *C12P 19/34* (2013.01)

(58) Field of Classification Search
CPC .......... C12P 19/34; C12Q 1/6869; C12N 9/96
See application file for complete search history.

(56) References Cited

U.S. PATENT DOCUMENTS

| | | |
|---|---|---|
| 5,001,050 A | 3/1991 | Blanco et al. |
| 5,198,543 A | 3/1993 | Blanco et al. |
| 5,576,204 A | 11/1996 | Blanco et al. |
| 5,723,584 A | 3/1998 | Schatz |
| 5,874,239 A | 2/1999 | Schatz |
| 6,410,228 B1 | 6/2002 | Schwartz et al. |

(Continued)

FOREIGN PATENT DOCUMENTS

| | | |
|---|---|---|
| WO | 2007075873 | 7/2007 |
| WO | 2007075987 A2 | 7/2007 |
| WO | 2007076057 A2 | 7/2007 |

OTHER PUBLICATIONS

Melissis, S. et al., J. Chromatogr., vol. 1122, pp. 63-75 (2006).*

(Continued)

*Primary Examiner* — Teresa E Strzelecka
(74) *Attorney, Agent, or Firm* — David C. Scherer

(57) ABSTRACT

Methods, Compositions, and Systems are provided for obtaining polymerase-template complex mixtures with improved levels of active polymerase. In some aspects active polymerase-template complex is separated by affinity for nucleoside phosphate moieties attached to a resin. In some aspects, a polymerase-template complex is exposed to reaction conditions in which a complementary strand to the template is produced. The extended reaction mixture is purified by reaction with a resin comprising nucleoside phosphate moieties. This purified mixture can be loaded onto substrates and can be used for further analyzes including single molecule sequencing.

18 Claims, 4 Drawing Sheets

(56) References Cited

U.S. PATENT DOCUMENTS

| | | |
|---|---|---|
| 6,917,726 B2 | 7/2005 | Levene et al. |
| 7,033,764 B2 | 4/2006 | Korlach et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,170,050 B2 | 1/2007 | Turner et al. |
| 8,658,364 B2 | 2/2014 | Pham et al. |
| 2001/0008114 A1 | 7/2001 | Falster et al. |
| 2004/0259082 A1 | 12/2004 | Williams |
| 2007/0238679 A1 | 10/2007 | Rank et al. |
| 2008/0195324 A1 | 8/2008 | Bushnell et al. |
| 2008/0199932 A1 | 8/2008 | Hanzel et al. |
| 2009/0105094 A1 | 4/2009 | Heiner et al. |
| 2009/0280538 A1 | 11/2009 | Patel et al. |

OTHER PUBLICATIONS

Melissis, S et al., Biotechnol. J., vol. 2, pp. 121-132 (2007).*

Melissis, S. et al., J. Chromatogr. Science, vol. 48, pp. 496-502 (2010).*

Federly, R.G. et al., J. Nucleic Acids, vol. 2010, Article ID 457176, pp. 1-15 (2010).*

Anderson et al., "Fluorescent Structural DNA Nanoballs Functionalized with Phosphate-Linked Nucleotide Triphosphates," NanoLetters (2010) 10:788-792.

Eid, et al., "Real-time DNA sequencing from single polymerase molecules" Science (2009) 323(5910):133-138.

Foquet et al. "Improved fabrication of zero-mode waveguides for single-molecule detection" J Appl Phys (2008) 103:034301-9.

Franklin et al., "Structure of the Replicating Complex of a Pol [alpha] Family DNA Polymerase" Cell (2001) 105:657-667.

Korlach et al., "Selective aluminum passivation for targeted immobilization of single DNA polymerase molecules in zero-mode waveguide structures" PNAS (2008) 105(4):1176-1181.

Korlach, et al., "Long, Processive Enzymatic DNA Synthesis Using 100% Dye-Labeled Terminal Phosphate-Linked Nucleotides," Nucleosides, Nucleotides and Nucleic Acids (2008) 27:1072:1083.

Levene et al., "Zero-mode waveguides for single-molecule analysis at high concentrations" Science (2003) 299 (5607):682-686.

Melissis et al., "One-Step Purification of Taq DNA Polymerase Using Nucleotide-Mimetic Affinity Chromatography," Biotechnol. J. (2007) 2:121-132.

* cited by examiner

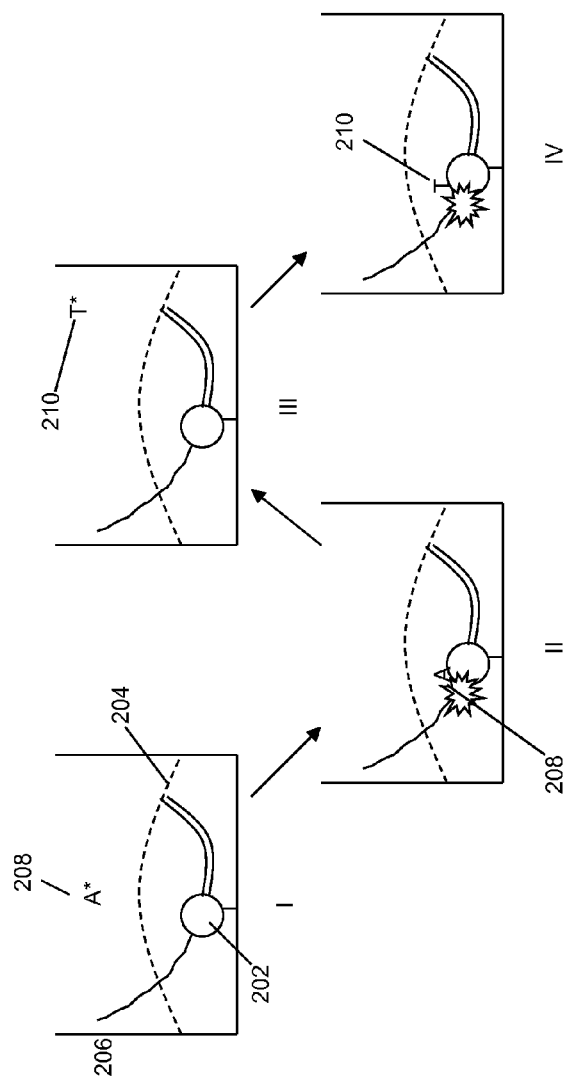
Figure 2A
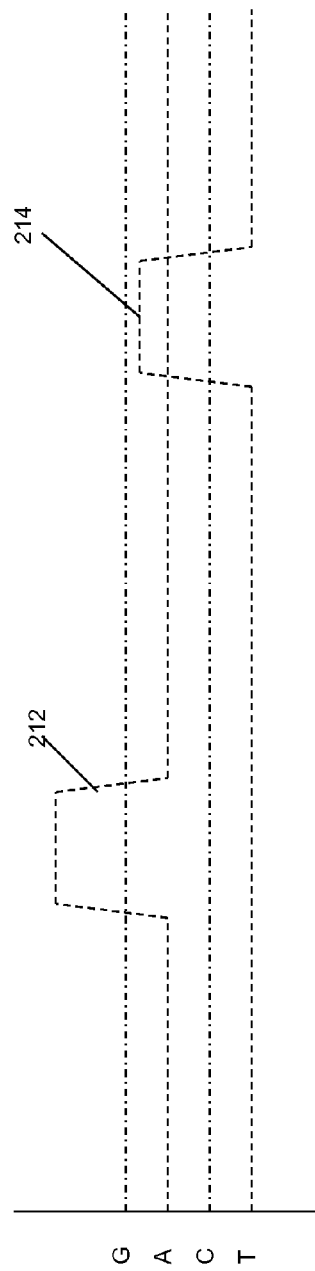
Figure 2B
Figure 2

PURIFIED POLYMERASE / TEMPLATE COMPLEXES

CROSS-REFERENCE TO RELATED APPLICATIONS

This application is a continuation application of U.S. patent application Ser. No. 13/233,585 filed on Sep. 15, 2011, which claims the benefit of Provisional Patent Application 61/385,376 filed on Sep. 22, 2010, the full disclosure of which is incorporated by reference herein in their entirety.

STATEMENT REGARDING FEDERALLY SPONSORED RESEARCH

Not Applicable.

BACKGROUND OF THE INVENTION

A number of techniques in molecular biology and molecular medicine now rely on analysis of single biological molecules. Such techniques include DNA and RNA sequencing, polymorphism detection, the detection of proteins of interest, the detection of protein-nucleic acid complexes, and many others. The high sensitivity, high throughput and low reagent costs involved in single molecule analysis make this type of analysis an increasingly attractive approach for a variety of detection and analysis problems in molecular medicine, from low cost genomics to high sensitivity marker analysis.

For example, single molecule DNA sequencing is useful for the analysis of large sets of related DNAs, such as those that occur in a genome. In certain of these methods, a polymerase reaction is isolated within an array of extremely small (typically optically confined) observation volumes that each permit observation of the enzymatic action of individual polymerases in each reaction/observation volume of the array, while the polymerase copies a template nucleic acid. Nucleotide incorporation events are individually detected, ultimately providing the sequence of the template molecule. This approach dramatically increases throughput of sequencing systems, and also dramatically reduces reagent consumption costs—to the point where personalized genomics is increasingly feasible.

The small observation volumes used for single molecule nucleic acid sequencing and other analysis methods are typically provided by immobilizing or otherwise localizing the polymerase (or other) enzyme within an optical confinement reaction/observation region, such as an array of extremely smalls wells as in an array of Zero Mode Waveguides (ZMWs), and delivering a template, primers, etc., to the reaction region.

While these methods of nucleic acid sequencing are providing dramatic improvements in the ability to obtain sequence information, there is a need for improvements in the throughput and yield of the systems. One area where improvement can be had is in raising the fraction of active polymerase-enzyme complex. Another area is the improvement in the fraction of observation volumes which contain a single active polymerase-template complex. The present invention provides these and other features that will be apparent upon complete review of the following.

BRIEF SUMMARY OF THE INVENTION

In some aspects the invention provides a method comprising: producing a reaction mixture comprising a polymerase enzyme complex having a polymerase enzyme and a template nucleic acid, the reaction mixture comprising reagents for template directed nucleic acid synthesis including nucleotides, nucleotide analogs or both; extending a complementary strand such that a portion of the polymerase enzyme complexes have complementary strands within a desired size range; purifying the reaction mixture to enhance the relative amount of polymerase enzyme complex having complementary strands within the desired size range; loading the purified reaction mixture onto a substrate.

In some embodiments a component of the reaction mixture is provided in a limiting amount that causes the extending of the complementary strand to halt when a portion of the polymerase enzyme complexes have complementary strands within the desired size range. In some embodiments the component provided in a limiting amount is one or more of the nucleotides or nucleotide analogs.

In some embodiments the reaction is halted at a time selected such that a portion of the polymerase enzyme complexes have complementary strands within a desired size range.

In some embodiments the reaction is halted using a metal salt. In some embodiments the metal salt comprises Ca++. In some embodiments the template nucleic acid comprises a circular nucleic acid strand. In some embodiments the template nucleic acid comprises a single circular strand of DNA having a self-complementary region, and having hairpin regions at the two ends of the complementary region. In some embodiments the template nucleic acid comprises sequences from a nucleic acid library.

In some embodiments the complex also comprises a primer hybridized to the nucleic acid template.

In some embodiments the desired size range of the complementary strand is from 100 bases to 100K bases. In some embodiments the desired size range of the complementary strand is from 1K bases to 20K bases.

In some embodiments purifying the reaction mixture comprises the use of size exclusion chromatography, gel permeation, or gel filtration chromatography. In some embodiments purifying the reaction mixture comprises the use of affinity chromatography. In some embodiments the polymerase enzyme complex is stabilized during purification with Ca++. In some embodiments the polymerase enzyme complex is stabilized during purification with one or more nucleotides or nucleotide analogs. In some embodiments the polymerase enzyme complex is stabilized during purification with Ca++ and one or more nucleotides or nucleotide analogs. In some embodiments the polymerase enzyme comprises a DNA polymerase. In some embodiments the DNA polymerase comprises a phi-29 type polymerase.

In some embodiments the polymerase enzyme comprises a reactive element for attachment to the substrate. In some embodiments the substrate onto which the purified reaction mixture is loaded comprises an array of reactive sites that react with the polymerase to immobilize the polymerase enzyme complex onto the substrate. In some embodiments the substrate onto which the purified reaction mixture is loaded comprises an array of nanoscale wells.

In some aspects the invention provides a composition comprising: a purified solution of polymerase enzyme complex, the enzyme complex comprising polymerase enzyme, template nucleic acid, and complementary strand, wherein the median size of the complementary strand is from about 10 percent to about 300 percent the median size of the median template nucleic acid.

In some embodiments the median size of the complementary strand is from 30 percent to about 200 percent the median size of the template nucleic acid. In some embodiments the polymerase enzyme comprises a DNA polymerase. In some embodiments the DNA polymerase comprises a phi-29 type polymerase. In some embodiments the polymerase enzyme comprises a reactive element for attachment to the substrate.

In some embodiments the median size of the complementary strand is from 100 bases to 100K bases. In some embodiments the median size of the complementary strand is from 1K bases to 20K bases. In some embodiments the purified solution has been produced using size exclusion chromatography or gel permeation chromatography.

In some embodiments the template nucleic acid comprises a circular nucleic acid. In some embodiments the template nucleic acid comprises a single circular strand of DNA having a self-complementary region, and having hairpin regions at the two ends of the complementary region.

In some embodiments the polymerase enzyme complex comprises one or more nucleotides or nucleotide analogs and divalent metal ions.

In some aspects the invention provides a method of obtaining an array of zero mode waveguides with greater than 37 percent of the zero mode waveguides having a single active polymerase comprising: producing a reaction mixture comprising a polymerase enzyme complex having a polymerase enzyme and a template nucleic acid, the reaction mixture comprising reagents for template directed nucleic acid synthesis including nucleotides, nucleotide analogs or both; extending a complementary strand such that a portion of the polymerase enzyme complexes have complementary strands within a desired size range; purifying the reaction mixture to enhance the relative amount of polymerase enzyme complex having complementary strands within the desired size range; loading the purified reaction mixture onto a substrate comprising an array of zero mode waveguides such that greater than 36 percent of the zero mode waveguides have a single active polymerase.

In some embodiments the array of zero mode waveguides comprises 10,000 to 1 million zero mode waveguides.

BRIEF DESCRIPTION OF THE DRAWINGS

FIG. 2A provides a schematic illustration of single molecule sequencing using polymerase-template complexes immobilized in an observation volume such as a ZMW.

FIG. 2B shows how signals measured from the observation volume can be used to identify added nucleotides in order to provide sequence information about the template nucleic acid.

DETAILED DESCRIPTION OF THE INVENTION

General

Figure 1:
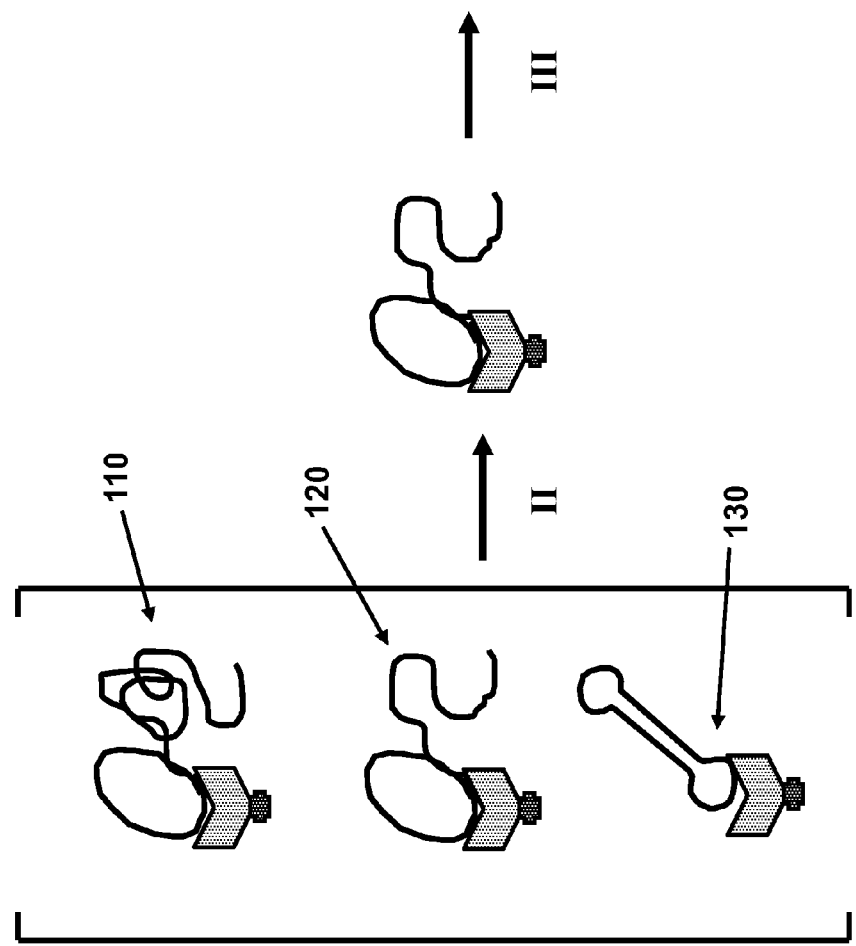
FIG. 1 shows a schematic illustrating the steps of extension of complementary strand from a polymerase-template complex, purification to produce purified polymerase-template complex mixtures for further analysis.

In some aspects, the invention is directed to improved compositions, methods, and systems for performing nucleic acid sequencing, and in particular single molecule nucleic acid sequencing. The invention is also directed to compositions and methods for obtaining populations of polymerase enzyme-template complexes having a high active fraction. The populations of polymerase enzyme-template complexes having high active fraction can be immobilized onto substrates for further analysis and observation.

Some approaches to single molecule sequencing involve first forming a complex between a polymerase enzyme and a nucleic acid template, then subsequently immobilizing the complex onto a substrate for further analysis, such as single molecule sequencing. See, for example U.S. Patent Application Publication No. 2009/0280538 and U.S. Patent Application Publication No. 2009/0105094. This can be done for a library of template nucleic acid fragments, whereby a nucleic acid sample is fragmented into a population or library of fragments, then the population of fragments is contacted with a solution of polymerase enzyme under conditions that lead to the formation of enzyme-template complexes. The complex is then attached to the substrate. This is generally accomplished by coupling of the enzyme to the substrate, as described, for example in U.S. Patent Application Publication No. 2008/0199932, PCT Publication No. WO2007075873, and U.S. Patent Application Publication No. 2007/0238679 which are incorporated by reference in there entirety for all purposes. The complex can alternatively be attached to the substrate through the template nucleic acid or the primer. We have found that in some cases, a portion of the formed complexes will are not active, in that the complexes will not add nucleotides to form a growing complementary strand to the template. This results in a fraction of active polymerases is less than 1. The active fraction that is obtained can depend on a number of parameters including the characteristics of the enzyme, the template, and the primers. For example, in some cases, the length of the template will affect the level of active fraction, with larger templates generally resulting in lower active fraction. Having a high level of active fraction can be important for obtaining high quality and high throughput nucleic acid sequencing. For example, in some cases, the polymerase enzyme complexes are loaded onto arrays of optical confinements such as zero mode waveguides wherein it is desired to have one and only one active polymerase enzyme complex per optical confinement. Where the active fraction is high, obtaining a high proportion of optical confinements having a single active polymerase complex can be more effective, allowing for higher throughput.

We have invented a method obtaining a higher fraction of active polymerase enzyme complex by providing the reagents for nucleic acid synthesis to a solution of polymerase-enzyme complexes, allowing nucleic acid synthesis to occur such that those active complexes will grow complementary strands. Once the nucleic acid synthesis is complete, we have found that we can separate the complexes that have grown complementary strands, and are thus active, from the inactive complexes that have not grown complementary strands. This separation can be done, for example based on the size of the complexes, for example using size exclusion chromatography or gel filtration chromatography. We have found that in order for the separation to be effectively carried out, the complex must be stable during the purification step. In some cases, we have found that the addition of stabilizing agents such as divalent metals including Ca++ can be used to stabilize the complexes during purification. We have also found that the addition of nucleotides including dATP, dGTP, dCTP, and TTP can be used to stabilize the complexes during purification. In other words, we found that pol-DNA-incoming nucleotide complex is more stable than pol-DNA complex. Metal is interacting with these three components and stabilize the complex. Once the separation is performed, the purified complexes can be loaded onto a substrate for further analysis. The purified complexes can be loaded onto arrays of optical confinements such as zero mode waveguides.

In addition to providing a population of enzyme-template complexes with higher levels of active fraction, the process provides a population of complexes that is within a specified size range, and in some cases relatively homogeneous in size. Obtaining size homogeneity can involve, e.g. selecting a relatively narrow size range in the purification step. Having a relatively homogeneous population of size can assist in obtaining consistent loading and reproducibility. The size range of the polymerase-template complexes can be selected such that once one polymerase enzyme complex is within a ZMW, it will tend to exclude the entry and/or the immobilization of a second polymerase enzyme complex within the ZMW. Having a first complex shield a second complex from immobilization allows for obtaining loading levels for single active polymerases above the level that can be obtained by statistical loading levels, that is, greater than a the levels obtained with a Poisson distribution. See, for example, U.S. Patent Application Publication No. 2010/0009872, and Provisional Patent Application 61/329,026, the contents of each of which are incorporated by reference herein for all purposes.

FIG. 1 shows a diagram outlining a method of the invention. To carry out the method, first a polymerase enzyme complex 100 is formed. The polymerase complex comprises a polymerase enzyme 101 and a template nucleic acid 102. The polymerase complex generally also comprises a primer hybridized to the template nucleic acid that will act as the starting point for the synthesis of the complementary strand. The template nucleic acid 102 can be a SMRT Bell™ DNA template as depicted in FIG. 1 having a central self-complementary double-stranded portion, and two single stranded hairpin regions at each end of the double-stranded portion. In such cases, polymerase 101 is generally a polymerase having strand displacement activity. For example, a phi29 type polymerase can be used. The polymerase enzyme 101 in the embodiment shown has a coupling agent 103 attached to it. The coupling agent 103 can be used to immobilize the enzyme to a substrate after purification of the complex. The coupling agent can comprise, for example avidin or streptavidin, which can be attached to the polymerase in a number of ways including via a bioitin linkage on the polymerase enzyme or as a fusion protein. The avidin or streptavidin coupling agent bound to the polymerase will bind to pre-formed biotin sites on the substrate to immobilize the polymerase.

While the polymerase enzyme-template complex in FIG. 1 is shown as being a single complex, in many instances, a plurality of complexes are formed. For example, the input nucleic acid may be a DNA sample that is fragmented into pieces, for example on the order of 2 KB to 4 KB in length, and SMRT Bell templates are formed by ligating universal hairpin regions on each end. The result is a mixture of templates template having universal hairpin regions, for example to act as priming sites, with each template generally having a unique double stranded region. This mixture of templates will result in a mixture of polymerase enzyme-template complexes, each complex generally comprising a different nucleic acid sequence.

In step (I) complex 100 is subjected to conditions for the polymerase enzyme mediated synthesis of a nucleic acid strand complementary to the nucleic acid template. The reaction mixture will generally comprise nucleotides, metals, essential salts, and buffers to control the pH. The active complexes will synthesize a nucleic acid strand complementary to the template nucleic acid. Where a primer is used the complementary strand will grow from the 3' end of the primer. FIG. 1 illustrates several sub-populations that will be generated after the synthesis reaction proceeds to a selected level of completion. The population will generally include inactive complexes which have undergone little to no nucleic acid synthesis 130, active complexes that have grown a nucleic acid strand within a desired size range 120, and in some cases, active complexes that have grown complementary strand that is larger than the desired size range 110.

The sequencing reaction can be halted at a desired time point by adding a reagent to reversibly stop polymerization or by changing the reaction conditions. There are a number of reagents that can be added to reversibly stop polymerization. Enzyme inhibitors, solvents and salts can be used. In some cases the addition of a metal cation such as Ca++ is added to halt the reaction. The addition of Ca++ can also be beneficial for stabilizing the polymerase enzyme complex during separation as described below. Other cations that can be used include Sr++, Ba++, or Ni++. In some cases, reagents that bind with or degrade synthesis reaction components can be used. For example, reagents which complex with or hydrolyze the nucleotides, or reagents that chelate the essential metals such as Mg++ or Mn++ can be used to halt the reaction. A change in condition such as lowering the temperature, reducing the metal concentration, reducing the nucleotide concentration, or changing the pH can also be employed for halting the reaction at a specific time point.

In a preferred embodiment, one or more reagents that are added for the polymerization reaction are added in limiting concentrations so that the reaction tends to stop when the reagents run out, or their concentration falls to a level at which the reaction is extremely slow. The concentration of the nucleotides in the reaction mixture can be provided such that the reaction halts or significantly slows down when the lengths of the complementary strands will be within a desired range. In some cases, both limiting concentrations of nucleotides and the addition of a reagent to halt the reaction at a specified time point is used. The combination can be beneficial as the limiting concentrations can be used to significantly slow down the reaction as reagents are depleted, then the addition of a compound is added to halt the reaction.

In step (II) a purification is carried out to exclude or minimize the relative amount of inactive complex. The purification can be carried out, for example, by gel permeation, size exclusion, or gel filtration chromatography, ion exchange chromatography or affinity purification including anti-DIG-IgG antibody beads and streptavidin beads. The desired size range may vary depending on the application. In some cases, for example, all complexes having complementary strand above a certain size will be retained. In some cases, such as illustrated in FIG. 1, only complexes within a desired size range 120 will be retained, and those above this size range 130 and below this size range 110 will be removed.

In step (III), the purified mixture of polymerase enzyme-template complexes is prepared for analysis, for example for use in nucleic acid sequencing. The purified mixture of polymerase complexes can be immobilized onto a surface for single molecule sequencing. For single molecule sequencing, it is generally desirable to have single molecules spaced apart on the surface such that the signals from such molecules are optically resolvable. In some cases, the purified polymerase enzyme complex mixture is diluted for immobilization onto a planar surface having a homogeneous layer of immobilization sites to which a complex will bind. In some cases, the substrate will have an array of specific functionalized regions to which the enzyme complexes will bind, surrounded by regions where binding will not occur. This allows for selectively placing the complexes at specific sites on the substrate as opposed to having a random distribution across the substrate. In some cases the polymerase enzyme complexes are onto a surface having an array of nanoscale apertures or zero mode waveguides, wherein it is desired to have a single active polymerase enzyme complex in each aperture or ZMW. An advantage of the present invention is that because the mixture has a higher fraction of active polymerase enzyme complexes, a higher yield of effective sites on the substrate are produced, and a higher proportion of nanoscale apertures or ZMWs can provide information. This results in a higher throughput system for nucleic acid sequencing.

Single Molecule Sequencing

The compositions, methods, and systems described herein can be used to improve the performance and through put of nucleic acid sequencing systems, specifically those which employ single molecule sequencing. Single molecule sequencing is based on reading the base sequence on single DNA molecules. There have been numerous approaches to single molecule sequencing, and many approaches utilize a polymerase enzyme complex immobilized on a substrate. In some cases the complex is attached to the surface through the polymerase, in other cases, the complex is attached by the template nucleic acid or the primer. The methods described herein can be used with single molecule sequencing methods of each of these types.

In some approaches to single molecule sequencing, only a single type of nucleotide is added to detect incorporation. These methods then require a cycling through of the various different types of nucleotides (e.g., A, T, G and C) to be able to determine the sequence of the template. Because only a single type of nucleotide is contacted with the complex at any given time, any incorporation event is by definition, an incorporation of the contacted nucleotide. These methods, while somewhat effective, generally suffer from difficulties when the template sequence includes multiple repeated nucleotides, as multiple bases may be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but are distinguishable by the presence on each type of nucleotide of a different optical label. Accordingly, such methods can use a single step to identify a given base in the sequence. In particular, all four nucleotides, each bearing a distinguishable label, are added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

In another process, single molecule primer extension reactions are monitored in real-time, to identify the continued incorporation of nucleotides in the extension product to elucidate the underlying template sequence. In one such single molecule real time (or SMRT™) sequencing, the process of incorporation of nucleotides in a polymerase mediated template dependent primer extension reaction is monitored as it occurs. In preferred aspects, the template/polymerase primer complex is provided, typically immobilized, within an optically confined region, such as a zero mode waveguide, or proximal to the surface of a transparent substrate, optical waveguide, or the like (see e.g., U.S. Pat. Nos. 6,917,726, and 7,170,050 and Published U.S. Patent Application No. 2007-0134128, the full disclosures of which are hereby incorporated herein by reference in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated. A schematic illustration of this sequencing process is shown in FIG. 2. As shown in FIG. 2A, an immobilized complex 202 of a polymerase enzyme, a template nucleic acid and a primer sequence are provided within an observation volume (as shown by dashed line 204) of an optical confinement, of e.g., a zero mode waveguide 206. As an appropriate nucleotide analog, e.g., nucleotide 208, is incorporated into the nascent nucleic acid strand, it is illuminated for an extended period of time corresponding to the retention time of the labeled nucleotide analog within the observation volume during incorporation which produces a signal associated with that retention, e.g., signal pulse 212 as shown by the A trace in FIG. 2B. Once incorporated, the label that attached to the polyphosphate component of the labeled nucleotide analog, is released. When the next appropriate nucleotide analog, e.g., nucleotide 210, is contacted with the complex, it too is incorporated, giving rise to a corresponding signal 214 in the T trace of FIG. 2B. By monitoring the incorporation of bases into the nascent strand, as dictated by the underlying complementarity of the template sequence, one can obtain long stretches of sequence information of the template. Further, in order to obtain the volumes of sequence information that may be desired for the widespread application of genetic sequencing, e.g., in research and diagnostics, higher throughput systems are desired.

By way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments. In preferred aspects, the various different complexes are provided arrayed upon a substrate. Such arrayed complexes may be provided within optically or structurally confined structures, e.g., zero mode waveguides, or they may be patterned on a surface. Alternatively, they may be randomly disposed over a surface but subjected to targeted arrayed illumination, or detection, such that only complexes within an array pattern on the surface are monitored. For purposes of discussion herein, both configurations are referred to herein as the monitoring of arrayed complexes, or the like.

Thus, while the systems of the invention may be used to provide a multiplex analysis of 10, 100, 1000, 5000 or the like discrete reaction regions on a substrate, in particularly preferred aspects, the invention will be employed to provide multiplex analysis of greater than 5000 discrete reaction regions, greater than 10,000 discrete reaction regions, greater than 20,000 discrete reaction regions, greater than 50,000 discrete reaction regions, and even greater than 100,000 discrete reaction regions, and up to 1,000,000 or more discrete reaction regions. For example, the number of reaction regions can be from about 1000 to about 1,000,000 reaction regions In addition to the shear number of reaction regions analyzable by the systems of the invention, it will be appreciated that in some cases, such reaction regions can be disposed at higher densities than previously employed, through the various advantages provided by the invention. For example, discrete reaction regions can be provided and observed at high densities without excessive interference or other problematic issues. Such densities can be, e.g., 1000, 10,000, 100,000, 1,000,000, 10,000,000, or more reaction regions per cm$^2$. For example the density can be between about 1000 and about 1,000,000 reaction regions per cm$^2$.

Polymerase Enzymes

Polymerase enzymes for use with the current invention can include polymerases mutated to have desirable properties for sequencing. For example, suitable enzymes include those taught in, U.S. Patent Application Publication Nos. 2007/0196846 filed Dec. 21, 2006; 2008/0108082, filed Oct. 23, 2006; 2010/0112645, filed Mar. 30, 2009, and 2010/0093555, filed Mar. 30, 2009, each incorporated herein by reference in their entirety for all purposes. The modified polymerases will generally have modified properties such as (e.g., decreased branch fraction formation, improved specificity, improved processivity, altered rates, improved retention time, improved stability of the closed complex, etc.). The polymerase enzymes useful in the invention will generally have strand displacement activity.

In addition, the polymerases can be further modified for application-specific reasons, such as to increase photostability, e.g., as taught in U.S. patent application Ser. No. 12/384,110 filed Mar. 30, 2009, to improve activity of the enzyme when bound to a surface, as described, e.g., in WO 2007/075987, and WO 2007/076057, each incorporated herein by reference in its entirety for all purposes, or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

DNA Polymerases

In many embodiments of the invention, DNA polymerases are employed. DNA polymerases are sometimes classified into six main groups based upon various phylogenetic relationships, e.g., with *E. coli* Pol I (class A), *E. coli* Pol II (class B), *E. coli* Pol III (class C), *Euryarchaeotic* Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47): 43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases. Other useful polymerases include BST polymerase and T4 DNA polymerase.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287.

RNA Polymerases

In some embodiments, the polymerase enzyme that is used for sequencing is an RNA polymerase. Any suitable RNA polymerase can be used including RNA polymerases from bacteria, eukaryotes, viruses, or archea. Suitable RNA polymerases include RNA PoI I, RNA PoI II, RNA PoI III, RNA PoI IV, RNA PoI V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors.

There are many proteins that can bind to RNAP and modify its behavior. For instance, GreA and GreB from *E. coli* and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e. they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or systems of the invention include RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Template Nucleic Acid.

It will be understood that the methods are applicable to various different kinds of nucleic acid templates, nascent strands, and double-stranded products, including single-stranded DNA; double-stranded DNA; single-stranded RNA; double-stranded RNA; DNA-RNA hybrids; nucleic acids comprising modified, missing, unnatural, synthetic, and/or rare nucleosides; and derivatives, mimetics, and/or combinations thereof.

The template nucleic acids of the invention can comprise any suitable polynucleotide, including double-stranded DNA, single-stranded DNA, single-stranded DNA hairpins, DNA/RNA hybrids, RNAs with a recognition site for binding of the polymerizing agent, and RNA hairpins. Further, target polynucleotides may be a specific portion of a genome of a cell, such as an intron, regulatory region, allele, variant or mutation; the whole genome; or any portion thereof. In other embodiments, the target polynucleotides may be, or be derived from mRNA, tRNA, rRNA, ribozymes, antisense RNA or RNAi. The template polynucleotide may be of any length, such as at between about 10 bases and about 100,000 bases, or between about 100 bases and 10,000 bases.

The template nucleic acids of the invention can include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. A nucleic acid can be e.g., single-stranded or double-stranded.

The nucleic acids used to produce the template nucleic acids in the methods herein (the target nucleic acids) may be essentially any type of nucleic acid amendable to the methods presented herein. In some cases, the target nucleic acid itself comprises the fragments that can be used directly as the template nucleic acid. Typically, the target nucleic acid will be fragmented and further treated (e.g. ligated with adaptors and or circularized) for use as templates. For example, a target nucleic acid may be DNA (e.g., genomic DNA, mtDNA, etc.), RNA (e.g., mRNA, siRNA, etc.), cDNA, peptide nucleic acid (PNA), amplified nucleic acid (e.g., via PCR, LCR, or whole genome amplification (WGA)), nucleic acid subjected to fragmentation and/or ligation modifications, whole genomic DNA or RNA, or derivatives thereof (e.g., chemically modified, labeled, recoded, protein-bound or otherwise altered). For example, a target nucleic acid may be bound to a protein involved in initiation of replication, e.g., .PHI.29 terminal protein p3 or adenovirus terminal protein, which are described in the art, e.g., in Blanco, et al. (1985) Proc. Natl. Acad. Sci. USA 82:6404-8; Penalva, et al. (1982) Proc. Natl. Acad. Sci. USA 79:5522-6; Inciarte, et al. (1980) J. Virol. 34:187-199; Harding, et al. (1980) Virology 104:323-338; Rekosh, et al. (1977) Cell 11:283-295; and Carusi, E. A. (1977) Virology 76:390-4, the disclosures of which are incorporated herein by reference in their entireties for all purposes.

The target nucleic acid may be linear, circular (including templates for circular redundant sequencing (CRS)), single- or double-stranded, and/or double-stranded with single-stranded regions (e.g., stem- and loop-structures). For example, certain preferred template structures are provided in U.S. Ser. No. 12/413,258, filed Mar. 27, 2009. The target nucleic acid may be purified or isolated from an environmental sample (e.g., ocean water, ice core, soil sample, etc.), a cultured sample (e.g., a primary cell culture or cell line), samples infected with a pathogen (e.g., a virus or bacterium), a tissue or biopsy sample, a forensic sample, a blood sample, or another sample from an organism, e.g., animal, plant, bacteria, fungus, virus, etc. Such samples may contain a variety of other components, such as proteins, lipids, and non-target nucleic acids. In certain embodiments, the target nucleic acid is a complete genomic sample from an organism. In other embodiments, the target nucleic acid is total RNA extracted from a biological sample or a cDNA library. As noted above, a target nucleic acid may be used directly in a template-directed sequencing reaction, or may be use to derive a population of nucleic acid templates suitable for use in such a reaction. For example, where whole genomic DNA is the target nucleic acid, it may be isolated from an organism, and fragmented to produce a population of template nucleic acids corresponding to the target nucleic acid. Further, target nucleic acid fragments or segments may be further subjected to size-selection (e.g., by chromatography, spin columns, or the like) to produce a pool of fragments within a desired size range (e.g., between about 500 and 5000 bp, or between about 700 and 2000 bp, or between about 500 and 20,000) or above a minimum size requirement, e.g., greater than about 250, 500, 1000, 2500, 5000, or 10,000 bp.

Isolation and/or purification of nucleic acids from samples is well known and routine in the art. Generally, nucleic acids can be extracted from a biological sample by a variety of techniques such as those described by Maniatis, et al., Molecular Cloning: A Laboratory Manual, Cold Spring Harbor, N.Y., pp. 280-281 (1982). A sample containing the target nucleic acid may be processed (e.g., homogenized or fractionated) in the presence of a detergent, surfactant, denaturant, reducing agent, and/or zwitterionic reagent by methods known in the art.

Circular Template/SMRT Bells

Circular templates are preferred templates for use in the invention. Circular templates can be duplicated over and over again, allowing for the growth of a complementary strand of any length while allowing for the sequence corresponding to the complementary strand to be sequenced at a later time. The preparation of circular templates is described, for example in U.S. Patent Application Publication Nos. 2008/0199874 filed Feb. 11, 2008; and 2009/0105094, filed Sep. 26, 2008, the contents of which are incorporated herein by reference in their entirety for all purposes.

Circular templates having a self-complementary double stranded region in the center and hairpin regions at each end, sometimes referred to as SMRT-Bells™ are also useful in the invention. SMRT Bell™ templates are described, for example, in U.S. Patent Application No. 2009/0280538, filed Mar. 27, 2009 which is incorporated herein by reference in its entirety for all purposes. A library of these templates can be produced by fragmenting a double stranded DNA sample into appropriate sized fragments, and ligating hairpin DNA segments to each end. The hairpin DNA segments are universal, allowing for them to be used as a universal priming site for all of the members of the library.

Components for Template Directed NA Synthesis

The methods of the invention include a step of template directed nucleic acid synthesis to grow a complementary strand within a desired size range. The extension of the complementary strands is generally carried out in a solution containing the components required for template directed nucleic acid synthesis. Conditions for template directed nucleic acid synthesis are well known in the art. The components generally include one or more primers, nucleotides, and cofactors including a divalent metal such as Mg++ or Mn++. A monovalent salt such as sodium and or potassium is also usually added in order to control the ionic strength of the medium. A buffer will generally be added to control the pH of the medium.

Polymerase enzymes generally require some sort of priming. While in some cases, the polymerase may be able to self prime, in most cases, a primer will be used as the initiation point for the synthesis of the complementary strand. Such primers may be random or designed primers, and may be essentially any type of nucleic acid amendable to the methods presented herein. For example, a primer may comprise DNA, RNA, cDNA, peptide nucleic acid (PNA), amplified and/or fragmented nucleic acid, or derivatives thereof (e.g., chemically modified, labeled, recoded, bound to one or more proteins, or otherwise altered). For example, the primer may be bound to a protein involved in initiation of replication. The primer may be single- or double-stranded, and/or double-stranded with single-stranded regions (e.g., stem- and loop-structures). Further, the target nucleic acid preparations comprising multiple primers bound thereto can be subjected to subsequent purification steps, e.g., to remove unbound primers or small target fragments, prior to initiation of primer extension. Such size-selective purifications, including but not limited to various size-exclusion spin columns, chromatography, and gel-based techniques, are well known to those of ordinary skill in the art (see, e.g., Maniatis, et al., Molecular Cloning: A Laboratory Manual, Cold Spring Harbor, N.Y., pp. 280-281 (1982)), and are commercially available, e.g., from Clontech (Mountain View, Calif.) and GE Healthcare (Sunnyvale, Calif.).

The primers for use as initiation sites may be chosen or designed in various ways, depending on the experimental objectives of the practitioner, e.g., which portions of a template (or template population) are to be targeted for complementary strand synthesis. For example, a first portion of a nucleic acid sample may be fragmented and used to prime a second "template" portion of the same nucleic acid sample where it is desired to prime across all nucleic acids in the sample. Alternatively, a portion of the nucleic acid sample can be selectively amplified to create amplified products of selected regions of the nucleic acids therein; such amplification products (or fragments thereof) used for priming the template population. For example, select portions of a template can be targeted by generating primers that hybridize only to certain regions of interest in the template, e.g., repetitive, intronic and/or exonic regions of a genomic nucleic acid sample, and may be designed to anneal to the sense strand, antisense strand, or both strands of the genomic nucleic acid sample. The ratio of primers relative to template nucleic acids can be adjusted to promote a preferred density of primers bound to the template. In certain embodiments, a set of primers is generated by fragmentation, e.g., of genomic DNA, a DNA library, or a mixture of nucleic acids from one or more sources. For example, genomic DNA from a first human population may be fragmented and used to prime genomic DNA from a second human population. Alternatively, genomic DNA from a human population may be fragmented and used to prime genomic DNA from a non-human population, or vice versa. A population of primers may also be generated by synthesizing multiple primers separately, and then creating preferred combinations of selected primers for specific experimental objectives. One of ordinary skill in the art will readily understand that a primer set may be designed is various ways and that the methods described herein should not be limited to any one method of primer design.

In certain aspects, one benefit of using random primers is that the sequence of the target nucleic acid need not be known. The length of the random primers used in the instant methods is typically six to nine bases, but may be adjusted by the skilled practitioner depending, e.g., on the target nucleic acid to which they must anneal. In certain preferred embodiments, nonomers (9-mers) have been shown to perform well as random primers. In other embodiments, the primers may be longer, e.g., between about 10 and 100 bases, 20 and 80 bases, 30 and 60 bases, or about 40-50 bases in length. In preferred embodiments, the size of the primers is small enough to favor annealing to the target nucleic acid over annealing to one another. In certain embodiments in which large nucleic acids are fragmented to produce primers, the primers will be a size characteristic of the fragmentation method used, for example, digestion with one or more nucleases (e.g., endonuclease(s), exonuclease (s), etc.), nebulizer, sonicator, and the like. The conditions under which fragmentation occurs can be modified to promote production of a desired size range of fragments, e.g., by changing reaction temperature, salt concentration, ion concentration, metal concentration, or nucleotide concentration by methods known in the art. In such embodiments, a particular range of fragments may be further isolated by methods well known in the art, e.g., gel purification, fractionation, etc. In some embodiments, the "randomness" of the primers may be altered, e.g., by changing the base composition, such as increasing the G-C content. In certain specific embodiments, the primers may be chemically modified. For example, they may contain one or more thiophosphate moieties at the 3' terminus to block the exonuclease activity of a polymerase, and/or they may have a photocaged 3' terminus to allow photo-initiation of the sequencing reaction. Although single-stranded primers are typically used, double-stranded or partially double-stranded primers may also be used, as noted above.

In some embodiments, the primers are synthesized by the practitioner of the methods presented herein using methods well known to those of skill in the art, e.g. using a DNA synthesizer such as those from Applied Biosystems (Foster City, Calif.). In other embodiments, the randomly synthesized primers are purchased from a third-party vendor, e.g., from New England Biolabs (Ipswich, Mass.) or Gene Link (Hawthorne, N.Y.).

In some cases, the primers may be designed to provide optimal positioning over the target to be sequenced. In particular, based upon the expected sequence of the target, primers may be provided that prime the target nucleic acid in desired locations, e.g., at regularly spaced intervals, within or proximal to particular sequence motifs, and the like. For example, in some cases, primers may be designed to fall within or immediately adjacent to known repetitive regions within a target nucleic acid, e.g., a genome, in order to provide sequence readouts in the repeat regions to aid in assembly of the sequence data. Similarly, primers may be designed to target exonic regions, intronic regions, repetitive regions, or other regions of interest in a target nucleic acid on the sense, antisense, or both strands of the target nucleic acid. Alternatively, primers may be targeted to multiple regions of interest to facilitate characterization and/or identification of particular genetic sequences, e.g., in diagnostic applications, or to target specific genomic regions, e.g., specific types of chromosomes or regions within whole chromosomes, e.g., telomeres, centromeres, sex chromosomes, etc.

In alternative embodiments of the invention, the underlying target nucleic acid and/or its fragments are used in place of exogenously introduced primers, e.g., the target is self-priming. In particular, in at least one aspect, a double-stranded target nucleic acid may be nicked in a plurality of locations, where each nick site provides a priming location for a strand-displacing polymerase. Alternatively, by employing a slow-cool process during an annealing step, one may increase the likelihood of intra-fragment hybridization. Because the probability of a perfect match of a single-stranded fragment and its complement is extremely low, it will result in fragments that are partially double-stranded. These partially double-stranded fragments then provide suitable priming sites for the polymerase. A variety of additional embodiments are readily practiced in accordance with the scope of the invention.

The nucleotides or nucleotide analogs used in the extension reaction (or in primer composition) or may be naturally-occurring or synthetic, and may include polynucleotide mimetics, e.g., methylated nucleic acids, peptide nucleic acids, modified peptide nucleic acids, locked nucleic acids, and any other structural moiety that can act substantially like a nucleotide or base, for example, by exhibiting base-complementarity with one or more bases that occur in DNA or RNA, and/or being capable of base-complementarity incorporation. In some embodiments, sequencing reactions for use with the methods presented herein include nucleotides that are tagged with a detectable label that is directly or indirectly detectable. Typically, the nucleotides will be naturally occurring nucleotides, for example dNTPs such as dATP, dGTP, dCTP, and dTTP for DNA and ATP, GTP, CTP, and UTP for RNA.

Metal cofactors are generally present in the reaction, and their type and concentration can be adjusted to optimize enzyme activity. Generally one of Mg++ or Mn++ will be used as a metal cofactor in the reaction. For a discussion of metal co-factor interaction in polymerase reactions, see, e.g., Arndt; et al., Biochemistry (2001) 40:5368-5375, which is also incorporated herein by reference in its entirety for all purposes.

Reaction conditions for carrying out nucleic acid synthesis are well known in the art. The conditions can be varied to control characteristics of the polymerase reaction. The polymerase reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors and nucleotide concentrations. Enzymatic reactions are often run in the presence of a buffer, which is used, in part, to control the pH of the reaction mixture.

Methods

In one aspect the invention provides methods of producing a substrate having polymerase enzyme-template nucleic acid complexes bound thereto. In some cases the method comprises first producing a reaction mixture comprising a polymerase enzyme complex having a polymerase enzyme and a template nucleic acid. The complex also typically comprises a primer bound to the template nucleic acid. The reaction mixture has reagents required for performing template directed nucleic acid synthesis. The reaction mixture includes a set of nucleotides, which are the building blocks for nucleic acid synthesis. Generally, unlabeled nucleotides are used, and natural nucleotides such as dNTPs or NTPs can be utilized. The polymerase reaction is performed such that a complementary strand is formed. This reaction generally will involve the extension of a primer annealed to the template nucleic acid. The reaction is carried out in order to allow complementary strands of the desired length to be formed. Some of the complexes will form complementary strands below the desired length indicating that the complexes have either very low or no activity. Some of the complexes may form complementary strands that are above the desired length. A purification step is then performed in order to separate the desired complexes from the rest of the reaction mixture. In some cases the separation is done only with the goal of removing the complexes with ether no or with very little activity. In some cases, the separation is carried out to produce a set of complexes having a desired size range, for example to facilitate loading, or to isolate the fraction of complexes that will synthesize nucleic acid at a desired range of rates. The purified complexes can then be used for analysis, including for example, immobilizing the complexes onto a substrate for single molecule sequencing.

The extending of the complementary strands is carried out as described herein or by methods known in the art. The amount of extension is generally controlled in order to obtain complementary strands within a desired size range. The desired size range will vary depending on the application. Typically the template nucleic acid will comprise a population of fragments which will have a size range and distribution. It is generally desired that the desired size range of the extended complexes be large enough that separation effectively removes complexes that have not been extended. In some cases, the median size of the extended complexes is greater than 10%, greater than 20%, greater than 30%, greater than 40%, greater than 50%, greater than 80%, greater than 100%, greater than 150%, greater than 200%, 300%, 400%, or greater than 500% the median size of the complexes before extension. The size can be expressed either as the mass of the complex, or as the mass or size of the complementary strand. In some cases the median length of the complementary strand after extension is between 100 bases and 100 kb. In some cases the median length of the complementary strand after extension is between 1 kb and 20 kb or 2 kb and 10 kb. In some cases the median length of the complementary strand after extension is between 2 kb and 5 kb.

The size range of the extended complementary strands can be controlled by adjusting the composition of the reaction mixture, by halting the reaction at a given time, or with a combination of these approaches. For example, by having some reagents present at limiting concentrations, the polymerase reaction will only proceed to a given point, and then the reaction will either stop, or will slow to the point where little or no appreciable growth of extension product occurs. In preferred embodiments, the nucleotides are provided in an amount which will result in a high proportion of extended complex in the desired size range. Determining the amount of nucleotide to produce extended product within a given size range is well understood in the art. In addition to controlling the amount of nucleotide, controlling the number of actively polymerizing sites can also be important. Calculations made by stipulating a given number of active polymerase molecules and a given number of nucleotide monomers can provide an estimate of the expected size range, and experiments can be performed to fine tune the conditions.

The polymerase reaction can be halted by any suitable method. The halting method should be reversible, such that the polymerase stops adding nucleotides at the desired time, but will be capable of polymerase activity at a later time following purification. In some cases reversible inhibitors of the polymerase are added. Methods for reversibly halting the enzyme include the addition of metal salts. In some cases, the metal salts used to halt the polymerase are divalent metals such as Ca++, Sr++, Ba++, or Ni++. Other inhibitors can be added, including inhibitors that block the active site of the polymerase, or reversibly denature the polymerase enzyme. In some cases, chelating agents, for example, chelating agents that bind Mn++ or Mg++ can be used. In some cases EDTA is used as a chelating agent to halt the polymerase reaction. In some cases EGTA is used as a chelating agent to halt the polymerization reaction. The polymerase reaction can also be halted by changing the conditions, for example by raising or lowering the temperature or raising, lowering the pH of the reaction, lowering the metal concentrations or lowering the nucleotide concentrations.

The polymerase reaction can also be halted by adding non-hydrolysable nucleotide, for example a nucleotide with modification on alpha or beta phosphate (Muller-Reichert et al. (1998) Structural changes at microtubule ends accompanying GTP hydrolysis: information from a slowly hydrolysable analogue of GTP, guanylyl (alpha,beta)methylenediphosphonate. See, e.g. Proc. Natl. Acad. Sci. USA 95 (7):3661.).

In some cases, the reaction is terminated using a reversible terminator. The reversible terminator can be an analog of a nucleic acid that terminates the chain when it is added, for example by having its 3' hydroxyl group blocked. The reversible terminator can be treated at a later time to form an end group on the complementary strand which is capable of continued nucleotide additions, for example by the removal of a group blocking the 3' hydroxyl. Reversible terminators are described, for example in Bentley et al., Nature. 2008 Nov. 6; 456(7218):49-51 and Bowers et al., Nat Methods. 2009 August; 6(8):593-5.

Once the reaction is halted, a purification step purifies the polymerase enzyme complexes that have produced product within a given size range from other components of the reaction mixture. The purification can be carried out on the basis of size, for example by size exclusion chromatography, gel filtration chromatography, or gel permeation chromatography. Size-exclusion chromatography (SEC) is a chromatographic method in which molecules in solution are separated based on their size (or their hydrodynamic volume). See e.g. Skoog, D. A.; Principles of Instrumental Analysis, 6th ed.; Thompson Brooks/Cole: Belmont, Calif., 2006, Chapter 28. SEC is usually applied to large molecules or macromolecular complexes such as proteins or other polymers. Other purification methods that can be used include gel electrophoresis, extraction, precipitation, ultracentrifugation, ion exchange chromatography, affinity chromatography and HPLC. For example, anion exchange columns can be used to separate DNA and RNA by size. See, for example columns available through Qiagen Corporation. Beads can be used for the separation, for example in conjunction with separation by affinity group. These can be used, for example when purifying with digoxigenin-anti-digoxigenin antibody or with biotin-streptavidin. Such systems are available through Roche Applied Sciences. Combinations of the purification methods can also be used. The mixture of extended complexes can be purified by methods that do not provide separation based directly on size. For example, the desired complexes can be purified by charge, hydrophobicity/hydrophilicity, zeta potential, or any other suitable physical or chemical property. The purified reaction mixture can be subjected to analysis in order to determine if the desired size range has been obtained.

In some cases, affinity groups can be incorporated into the complementary strand during its synthesis. This can be done, for example, by including some modified nucleotides having affinity groups into the reaction mixture for the synthesis of the complementary strand.

Where chromatographic methods are used, fractions can be collected, then combined or discarded in order to obtain a mixture of polymerases with the desired range of sizes. In some cases all of the polymerase complexes above a certain size will be retained. In some cases, only polymerase complexes having a size range within an upper or lower cut off will be retained. In addition to enhancing the level of active polymerase, the purification also separates the polymerase complexes from components that are not desired in the analysis reaction. For example, the purification can remove or reduce the amount of free template, free primer, and other components of the extension reaction mixture.

In some cases, we have found that it is desirable to add one or more agents that stabilize the complex during purification. There are certain sets of conditions that tend to favor the stability of the enzyme-template complex. Without the use of the appropriate conditions, the polymerase-template complex my tend to dissociate, lowering the yield of active polymerase complex. We have found, for example, that the addition of a stabilizing divalent metal such as $Ca^{++}$, $Sr^{++}$, $Ba^{++}$, $Ti^{++}$, or $Ni^{++}$ can provide such stability during purification. The divalent metal ions can be removed before using the polymerase complex in an analysis reaction such as sequencing. In particular, we have found that the addition of $Ca^{++}$ is advantageous. Note that these metals have the advantage that they can also be used to halt the polymerase reaction as described above, and be retained during purification to provide stability. In some cases, the presence of one or more nucleotides will enhance the stability of the polymerase-template complex. While not being bound by theory, it is believed that the stabilizing cation such as $Ca^{++}$ acts to stabilize the ternary pol-DNA-incoming nucleotide complex, for example by stabilizing the incoming nucleotide's interaction with the pol and template DNA. See, for example, Franklin, et al., Cell, Vol. 105, 657-667, 2001. Nucleotides added for stabilization can be incorporable or non-incorporable nucleotides. They can be natural nucleotides, or nucleotide analogs. The nucleotide analogs generally have added groups not present in the natural nucleotides, but nonetheless are able to be incorporate by a polymerase enzyme. Nucleotide analogs useful in sequencing are well known in the art. See, for example U.S. patent application Ser. No. 11/645,223 filed Dec. 21, 2006 and U.S. patent application Ser. No. 12/403,090 filed Mar. 12, 2009. In some cases, the nucleotide analog added to improve stability will be the same type of nucleotide analog that is used during the analysis reaction. Other additives can be included in order to further stabilize the composition including glycerol, betaine, polyethylene glycol and surface active agents such as Tween20.

The purified polymerase enzyme-template complex can then be used for biochemical analyses. The polymerase enzyme complexes can be used for nucleic acid sequencing, and in particular, can be used for single molecule nucleic acid sequencing. In some cases the purified complexes are immobilized onto a substrate for nucleic acid sequencing. The immobilization of polymerase enzymes onto surfaces is known in the art.

The polymerase template complexes can in some cases be immobilized onto a transparent or silica-based region of the surface of a substrate. These polymerase-template complexes can thereby be disposed into reaction and or observation regions, such as within an optical confinement.

The polymerase-template complexes can be attached to coupling agents selectively placed onto the transparent or silica-based portions of the surface as described above. A variety of chemistries are available for specifically attaching a polymerase-template complex to the coupling agents bound to the surface.

For example, where biotin is bound to the transparent or silica-based regions of the surface, this surface can be used to attach the polymerase-template complex using a binding agent such as streptavidin, which has a very high affinity for biotin. In one approach, the polymerase-template complex has a biotin tag which can then be attached to the surface using an intermediate binding agent, e.g., streptavidin, which acts to bind to both the surface and the polymerase-template complex. In some cases, streptavidin is attached directly to the polymerase.

For a description of polymerases and other enzymes that are active when bound to surfaces, which is useful in single molecule sequencing reactions in which the enzyme is fixed to a surface (e.g., to a particle or to a wall of a reaction/ observation region, e.g., in a ZMW), e.g., conducted in a ZMW, see Hanzel et al. ACTIVE SURFACE COUPLED POLYMERASES, WO 2007/075987 and Hanzel et al. PROTEIN ENGINEERING STRATEGIES TO OPTIMIZE ACTIVITY OF SURFACE ATTACHED PROTEINS, WO 2007/075873). For a description of polymerases that can incorporate appropriate labeled nucleotides, useful in the context of sequencing, see, e.g., Hanzel et al. POLYMERASES FOR NUCLEOTIDE ANALOGUE INCORPORATION, WO 2007/076057. For further descriptions of single molecule sequencing applications utilizing ZMWs, see Levene et al. (2003) "Zero Mode Waveguides for single Molecule Analysis at High Concentrations," Science 299: 682-686; Eid et al. (2008) "Real-Time DNA Sequencing from Single Polymerase Molecules" Science DOI: 10.1126/science. 322.5905.1263b; Korlach et al. (2008) "Selective aluminum passivation for targeted immobilization of single DNA polymerase molecules in zero-mode waveguide nanostructures" Proceedings of the National Academy of Sciences U.S.A. 105(4): 1176-1181; Foquet et al. (2008) "Improved fabrication of zero-mode waveguides for single-molecule detection" Journal of Applied Physics 103, 034301; "Zero-Mode Waveguides for Single-Molecule Analysis at High Concentrations" U.S. Pat. No. 7,033,764, U.S. Pat. No. 7,052,847, U.S. Pat. No. 7,056,661, and U.S. Pat. No. 7,056,676, the full disclosures of which are incorporated herein by reference in their entirety for all purposes. In some cases, the enzyme can be covalently attached to the substrate through functional groups on the enzyme such as amine, carboxylate, or thiol groups, for example with NHS or maleimide linking chemistry.

In order to attach an enzyme to the surface, binding elements can be added to the polymerase (recombinantly or, e.g., chemically) including, e.g. biotin, digoxigenin, inosine, avidin, GST sequences, modified GST sequences, e.g., that are less likely to form dimers, biotin ligase recognition (BiTag) sequences, S tags, SNAP-tags, enterokinase sites, thrombin sites, antibodies or antibody domains, antibody fragments, antigens, receptors, receptor domains, receptor fragments, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Further details on attaching tags is available in the art. See, e.g., U.S. Pat. Nos. 5,723,584 and 5,874,239 for additional information on attaching biotinylation peptides to recombinant proteins.

Isolation of Active Complex Using Affinity

In some aspects, the invention provides for obtaining isolated active polymerase enzyme-template complex using an affinity column. For example, it is known that a nucleotide mimic affinity column can be used to purify a polymerase enzyme. See, e.g. Sotirios et al. Biotechnol. J., 2, 121-132, 2007. In the instant invention, a nucleotide is attached to the resin in a column through its polyphosphate portion to produce a nucleotide-phosphate affinity column. This column can be used to isolate active polymerase enzyme-template complex from inactive complex and other components in the solution. While such substrate-affinity columns have been used to purify active enzyme, here we provide for the purification of not just enzyme, but of active enzyme-template complex. We are able to purify the complex and not just the enzyme by controlling the conditions throughout the purification process such that the enzyme-template complex remains intact. In order to do this, a first set of conditions is selected under which the polymerase-template complex binds to the nucleotide-phosphate column. Washing is then carried out to remove undesired components including inactive complex. Then a second set of conditions is selected under which the enzyme-nucleic acid complex releases from the column, yet remains intact. We have found that this can be accomplished by controlling the components in the reaction mixture and the reaction conditions, including temperature. For example, controlling the ionic strength and the concentration of key ions can be used to strengthen or weaken the binding between the complex and the nucleotide phosphate column. In some cases, the binding of the complex to the column can be carried out in the presence of strontium ion, and the release of the complex can be accomplished by the addition of a chelator such as EDTA. Many chelators are known which will complex ions in solution such a strontium ion. Other chelators include DTPA, NTA, and EGTA. The ions Mg++ and Mn++ can also be added to promote elution of the complex.

A suitable nucleotide phosphate affinity column can be produced by reacting a nucleotide phosphate functionalized at its terminal phosphate to couple it to groups on the column. Methods for adding desired groups to affinity columns are well known in the art. For example, an Agarose resin functionalized with N-hydroxysuccinimide (NHS) groups can be reacted with a nucleoside triphosphate having attached to its terminal phosphate an alkyl amine group having e.g. from 2 to 20 carbons. The amine can react with the NHS groups on the column to add the nucleotide moieties. Any suitable nucleotide polyphosphate, for example having from 1 to about 8 phosphate units can be used. The nucleoside can be any natural nucleoside or a nucleoside analog. The nucleoside could be, for example deoxyadenosine.

In some aspect, the invention provides a method for isolating active polymerase enzyme nucleic acid complexes comprising: contacting a polymerase enzyme with a template nucleic acid to produce a population of polymerase enzyme nucleic acid complexes in solution, at least some of which are active; exposing the population of polymerase enzyme nucleic acid complexes with a resin having nucleoside phosphate moities attached thereto under conditions whereby the active polymerase enzyme nucleic acid complexes bind to the resin; washing the resin to remove components not bound to the resin; and eluting under conditions whereby the active polymerase enzyme nucleic acid complex releases from the resin, thereby isolating the active polymerase enzyme nucleic acid complex. Typically, the resin, which can be, for example, agarose, is contained within a column.

In some embodiments the exposing step is carried out in the presence of strontium ion. In some embodiments the eluting step is carried out in the presence of a chelating agent such as EDTA. In some embodiments the eluting step is carried out in the presence of magnesium ion or manganese ion.

Compositions

In some aspects, the invention is directed to compositions. These compositions can be of use in carrying out the methods of the invention. The compositions of the invention include purified solutions of enzyme template complex having active polymerase complexes with complementary strands that have been grown by the polymerase, and are still capable of further growth. The purified solutions are generally prepared by providing a polymerase-template-primer complex, and extending the primer using nucleotides to produce a complementary strand to the template nucleic acid. The extension of the complementary strand continues until the complementary strand grows to within a desired length range. These reaction mixtures are prepared and purified as described herein to produce the purified compositions of the invention.

The purification method used to produce the compositions can be any suitable purification method, for example, the methods described herein. The purification can be carried out on the basis of size, for example by size exclusion chromatography, gel filtration chromatography, or gel permeation chromatography. Other purification methods that can be used include gel electrophoresis, extraction, precipitation, ultracentrifugation, ion exchange chromatography, affinity chromatography and HPLC.

Typically the template nucleic acid will comprise a population of fragments which will have a size range and distribution. It is generally desired that the desired size range of the extended complexes be large enough that separation effectively removes complexes that have not been extended. A polymerase-template complex produced by the reaction and subsequent purification can produce polymerase-template complex in the desired size range in which the median size of the extended complexes is greater than 10%, greater than 20%, greater than 30%, greater than 40%, greater than 50%, greater than 80%, greater than 100%, greater than 150%, greater than 200%, 300%, 400% or greater than 500% the median size of the complexes before extension. The size can be expressed either as the mass of the complex, or as the mass or size of the complementary strand. In some cases, the median size of the extended complementary strand is greater than 10%, greater than 20%, greater than 30%, greater than 40%, greater than 50%, greater than 80%, greater than 100%, greater than 150%, greater than 200%, 300%, 400% or greater than 500% the median size of the template before extension. Thus in some cases, in the compositions of the invention, the median size of the extended complementary strand is from about 10% to about 500% greater than the median size of the template strand. In some cases the median size of the extended complementary strand is from about 10% to about 300% greater than the median size of the template strand. In some cases the median size of the extended complementary strand is from about 30% to about 200% greater than the median size of the template strand. In some cases the composition comprises a mixture of polymerase-template complexes in which the median length of the complementary strand after extension and purification is between 100 bases and 100 kb. In some cases the median length of the complementary strand after extension is between 1 kb and 20 kb. In some cases the median length of the complementary strand after extension is between 2 kb and 5 kb.

In some aspects, the invention provides a composition comprising: a purified solution of polymerase enzyme complex, the enzyme complex comprising polymerase enzyme, template nucleic acid, and complementary strand, wherein the median size of the complementary strand is from about 10 percent to about 300 percent the median size of the template nucleic acid. In some cases the median size of the complementary strand is from about 30 percent to about 200 percent the median size of the template nucleic acid.

The polymerase enzyme in the complex can comprise any suitable polymerase enzyme described here or known in the art. In some cases, the polymerase is a DNA polymerase. Generally, a polymerase having relatively high processivity is desirable. The DNA polymerase can be, for example a phi-29 type polymerase. The polymerase enzyme will in some cases have functionality for subsequent immobilization of the enzyme onto a substrate. Thus in some cases the enzyme may comprise a reactive site or reactive element for attachment to the substrate. Reactive binding elements include, for example, biotin, avidin, GST sequences, modified GST sequences, e.g., that are less likely to form dimers, biotin ligase recognition (BiTag) sequences, S tags, SNAP-tags, enterokinase sites, thrombin sites, antibodies or antibody domains, antibody fragments, antigens, receptors, receptor domains, receptor fragments, or combinations thereof. The reactive site could comprise biotin or streptavidin or both.

Preferred compositions comprise a circular template nucleic acid. The circular templates can be single stranded or double stranded or have both single stranded and double stranded portions. Circular templates having a self-complementary double stranded region in the center and hairpin regions at each end, referred to as SMRT-Bells™ are useful.

In some cases, the composition also comprises a primer as described herein.

Obtaining Greater Than Statistical Loading of Nanoscale Apertures

The small observation volumes used for single molecule nucleic acid sequencing and other analysis methods are typically provided by immobilizing or otherwise localizing the polymerase (or other) enzyme within an optical confinement reaction/observation region, such as an array of nanoscale wells as in an array of Zero Mode Waveguides (ZMWs), and delivering a template, primers, etc., to the reaction region. One difficulty in performing single molecule analyses occurs in loading the reaction/observation region of single molecule analysis devices with the molecules of interest (e.g., template or other analyte and/or enzyme). Loading two or more molecules of interest into a ZMW or other small observation volume tends to complicate any analysis of signals observed from double (or more than double)-loaded region. This is because two (or more) sets of signals may simultaneously be observed from the ZMW or other observation volume, meaning that the signals from the ZMW would have to be deconvoluted before data from the observation region could be used. More typically, data from double(+) loaded ZMWs can be recognized by various data analysis methods, and data from mis-loaded ZMWs or other relevant observation volumes is simply discarded.

To reduce the incidence of multiple molecule loading events in the relevant reaction/observation volume(s) of the array, it is typical in the art to substantially "under-load" the array with the analyte molecules of interest. Random distribution of molecules into the array results in one or fewer molecules being loaded into most reaction/observation volumes when fewer than 37% of all observation volumes are loaded. This type of loading is referred to as "Poisson-limited" analyte loading, meaning that few enough molecules are added to the array so that a Poisson-style random statistical distribution of the analytes into the array results in one or fewer analytes per observation volume in most cases. In the ZMW context, state of the art yields for single-molecule occupancies of approximately 30% have been obtained for a range of ZMW diameters (e.g., 70-100 nm). See, Foquet (2008), above. For this degree of loading, about 60% of the ZMWs in a typical ZMW array are not loaded (e.g., have no analyte molecules).

Various approaches have been described for obtaining single active polymerase loadings at greater than the 37% attainable by Poisson-limited loading. See, e.g. U.S. Patent Application No. 2010/0009872 filed Mar. 30, 2008 which is incorporated herein by reference in its entirety for all purposes. One method to obtain such loading levels involves producing structures of a size such that when one structure enters the ZMW, it impedes the entry of a second structure into the ZMW. The methods of the invention can be used to produce such structures by controlling the size of the extended complex first by controlling the growth of the complementary strand, followed by purification to select only the subset of complexes having sizes within the desired range.

The ZMWs for use in single molecule sequencing generally range in size from about 50 nm to about 200 nm. The methods of the present invention allow for producing polymerase enzyme complexes having dimensions on this order. The complementary nucleic acid that is formed can in some cases adopt a random coil configuration. The size of the random coil is dependent on the condition of the medium. Changes in the condition of the medium can be used to control the size of the polymerase enzyme complex. The size can be controlled by adjusting the ionic strength, the pH, or the polarity of the medium. Additives such as solvents, e.g. polar aprotic solvents can be used. In addition, chelating agents and intercalators can be employed for controlling the size of the polymerase enzyme complexes. When providing additives to control the size for loading it is generally desirable to select additives that will not adversely affect the nucleic acid sequencing reaction, or that can be removed prior to sequencing.

In some aspects, the invention provides a method of obtaining an array of zero mode waveguides with greater than 37 percent of the zero mode waveguides having a single active polymerase first forming a mixture of polymerase enzyme complexes in the desired size range by forming a reaction mixture comprising a polymerase enzyme complex having a polymerase enzyme and a template nucleic acid, where the reaction mixture has reagents for template directed nucleic acid synthesis including nucleotides, nucleotide analogs or both. The reaction results in extending a complementary strand. The reaction is carried out in such a manner that a portion of the polymerase enzyme complexes have complementary strands within a desired size range. This can be done by limiting the input of reagents such as nucleotides, by halting the reaction at a desired time point, or both. After forming the polymerase enzyme complexes with extended complementary strand, the reaction mixture is purified under conditions in which it the complex remains stable. The purification, for example with gel permeation chromatography or size exclusion chromatography can produce a mixture of complexes having a relatively narrow size range where the size range is selected to inhibit a second complex from entering a ZMW once a first complex has entered. The purified complexes are loaded onto a substrate comprising an array of zero mode waveguides. By selecting the appropriate conditions for loading the substrate and controlling the size of the size of the ZMWs, a substrate can be formed where greater than 37 percent of the zero mode waveguides have a single active polymerase.

Figure 3:
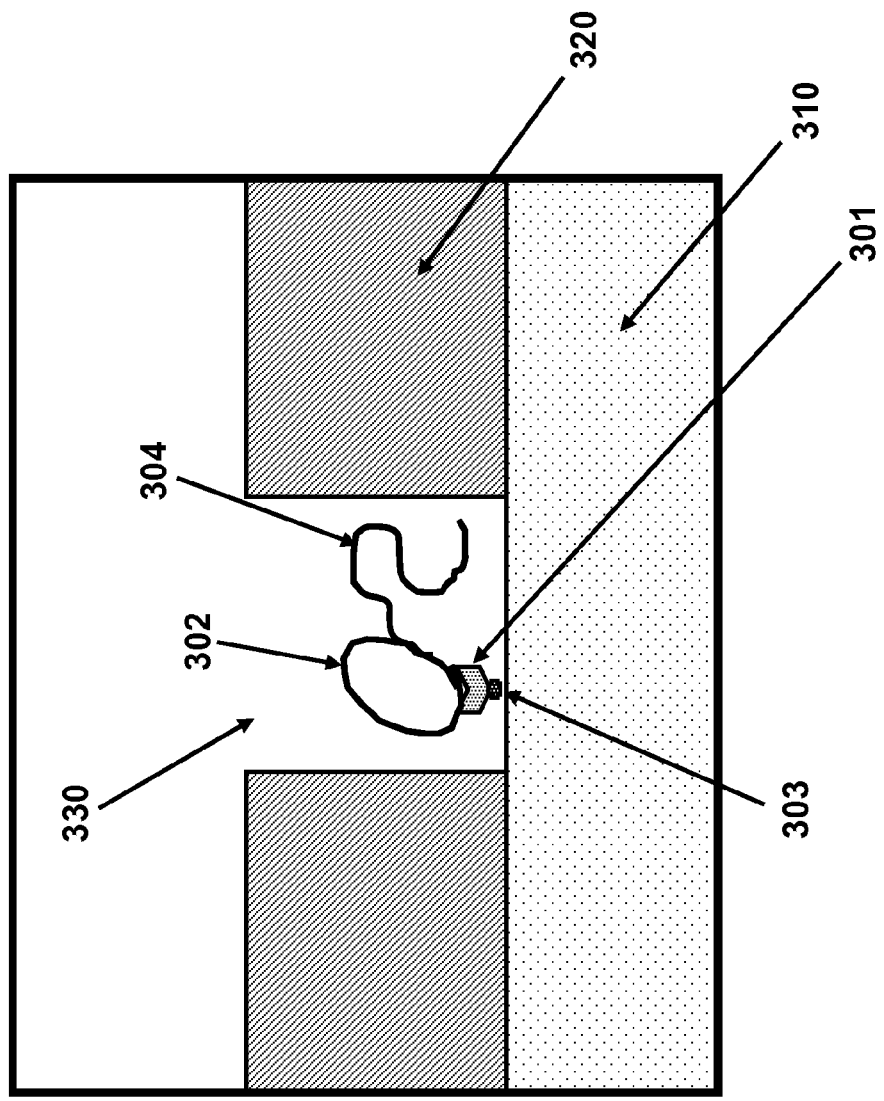
FIG. 3 is a schematic drawing illustrating the use of an extended polymerase-template complex that fits into an observation volume and hinders the attachment of a second polymerase-template complex within that volume.

FIG. 3 illustrates the binding of an extended polymerase-template complex that is of a size that will obstruct the binding of a second polymerase-template complex, allowing for high loadings of active polymerase-template complexes. The polymerase enzyme-template complex comprises a polymerase enzyme 301, having a reactive element 303 for binding to the substrate, a template nucleic acid 302, and an extended complementary strand 304. The polymerase enzyme-template complex is bound to the transparent substrate 310 with a nanoscale well or ZMW 330, which comprises a nanoscale hole in cladding layer 320. The complex has been purified to select complexes having a size that fits into ZMW 330, and having a size that hinders or blocks the entry of another polymerase-template complex. As would be understood by one of skill in the art, the drawing of FIG. 3 provides an illustration of the invention, and that the molecules and structures are not necessarily drawn to scale.

This method is generally performed on a ZMW array having a relatively large number of ZMWs. The number of ZMWs can range, for example from about 10,000 to 1 million zero mode waveguides, or to more than a million zero mode waveguides on the same substrate.

EXAMPLES

Example 1: Production of the Polymerase-Template Complex with Extended Template Into a reaction tube was added 200 nm of a 70 nt circular template, primer, 100 nM of phi-29 polymerase complexed with streptavidin, 1 mM of MnOAc, 100 µM each of dATP, dCTP, dGTP, and dTTP, 50 mM of ACES buffer (pH 7.1) and 75 mM of potassium acetate. The reaction volume was brought to 100 µL, and the mixture was incubated at 37° C. for 1 hour. This resulted in the formation of the polymerase enzyme-template complex. The 70 nt circular template was prepared as described in Nucleosides, Nucleotides and Nucleic Acids, 27:1072:1083, 2008. At the end of the 1 hour time period, 10 mM of $CaCl_2$ was added to halt the reaction and stabilize the complex. The, tube containing the reaction mixture was put onto ice.

Example 2: Purification of the Polymerase-Template Complex

Figure 4:
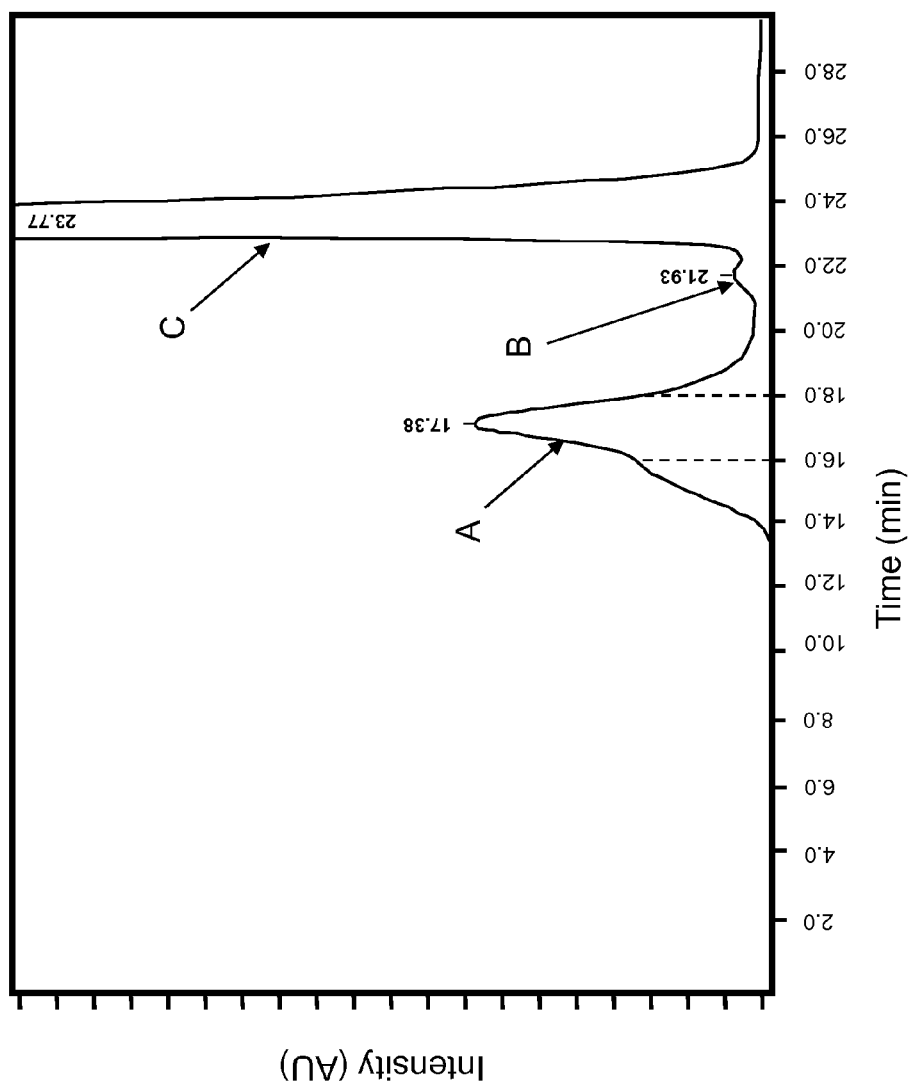
FIG. 4 shows a trace from a Gel Filtration Chromatography run illustrating the separation of the polymerase enzyme complex from other components and the selection of a range of sizes of polymerase enzyme complexes.

Onto a TSKgel G-DNA-PW Gel Filtration Chromatography column from Tosoh Bioscience LLC was loaded 100 µL of the reaction mixture from Example 1. Gel filtration was carried out using a solution comprising 10 mM Tris-Cl (pH7.5), 100 mM NaCl, 10 mM CaCl2, and 1 µM of the four dNTPs. The elution was carried out at 0.4 mL/min. FIG. 4 shows a plot of intensity versus time for the run. Peak A corresponds to polymerase-template complex including primer. Peak B corresponds to free 70 nt template nucleic acid. Peak C corresponds to the dNTPs, free polymerase, Mn, and other relatively small components of the mixture. The fraction between about 16 min and about 18 minutes of elution time was retained. This fraction is a purified mixture of polymerase-template complex having a desired size range.

Example 3: Immobilizing the Purified Polymerase-Template Mixture Onto a Substrate and Sequencing A portion of the purified mixture was loaded onto Zero Mode Waveguide arrays having biotin immobilized within the ZMWs for the attachment of the polymerase-template complexes thought the streptavidin moiety on the polymerase. Sequencing was carried out as described in Eid et al., Science, vol. 323, pages 133-138, 2009 and supporting material. Sequencing of the template nucleic acid was successfully carried out.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, particle delivery can be practiced with array well sizing methods as described. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method for isolating active polymerase enzyme nucleic acid complexes comprising:
   contacting a phi-29 DNA polymerase enzyme or a modified form thereof with a primer-hybridized template nucleic acid to produce a population of polymerase enzyme nucleic acid complexes in solution, at least some of which are active;
   exposing the population of polymerase enzyme nucleic acid complexes with a resin having nucleoside polyphosphate moieties attached thereto in the presence of a stabilizing divalent cation under conditions whereby the active polymerase enzyme nucleic acid complexes bind to the nucleoside polyphosphate moieties, wherein the divalent cation is $Ca^{++}$, $Sr^{++}$, $Ba^{++}$, $Ti^{++}$, or $Ni^{++}$;
   washing the resin to remove components not bound to the resin; and
   eluting the active polymerase enzyme nucleic acid complexes bound to the nucleoside polyphosphate moieties attached to the resin by contacting the resin with a chelating agent, thereby isolating the active polymerase enzyme nucleic acid complexes.

2. The method of claim 1 wherein the resin is contained within a column.

3. The method of claim 1 wherein the resin comprises a bead.

4. The method of claim 1 wherein the stabilizing divalent cation is $Sr^{++}$.

5. The method of claim 1 wherein the chelating agent is EDTA.

6. The method of claim 1 wherein the resin comprises agarose.

7. The method of claim 1 further comprising extending complementary strands of at least a portion of the active polymerase enzyme nucleic acid complexes prior to the exposing step.

8. The method of claim 1 further comprising loading the isolated active polymerase enzyme nucleic acid complexes onto a substrate.

9. The method of claim 8 wherein the phi-29 DNA polymerase enzyme or modified form thereof comprises a reactive element for attachment to the substrate.

10. The method of claim 8 wherein the substrate comprises an array of reactive sites that react with the phi-29 DNA polymerase enzyme or modified form thereof to attach the isolated active polymerase enzyme complexes to the substrate.

11. The method of claim 8 wherein the substrate onto which the purified reaction mixture is loaded comprises an array of nanoscale wells.

12. The method of claim 1 wherein the phi-29 DNA polymerase enzyme or modified form thereof is a wild-type phi-29 DNA polymerase enzyme.

13. The method of claim 1 wherein the phi-29 DNA polymerase enzyme or modified form thereof is a modified phi-29 DNA polymerase enzyme.

14. The method of claim 13 wherein the modified phi-29 DNA polymerase enzyme is exonuclease deficient.

15. The method of claim 1 wherein the nucleoside polyphosphate moieties comprise from 3 to 8 phosphate units.

16. The method of claim 1, wherein the template nucleic acid is a circular nucleic acid.

17. The method of claim 16, wherein the circular nucleic acid comprises a self-complementary region and hairpin regions at the ends of the complementary region.

18. The method of claim 1 wherein the stabilizing divalent cation is $Sr^{++}$, the chelating agent is EDTA, the nucleoside polyphosphate moieties comprise from 3 to 8 phosphate units, and the template nucleic acid is a circular nucleic acid.

* * * * *